US012239457B2

(12) United States Patent
Greene et al.

(10) Patent No.: US 12,239,457 B2
(45) Date of Patent: Mar. 4, 2025

(54) METHOD FOR MONITORING ADHERENCE TO MEDICATION

(71) Applicant: ROYAL COLLEGE OF SURGEONS IN IRELAND, Dublin (IE)

(72) Inventors: Garrett Greene, Dublin (IE); Richard Costello, Dublin (IE); Imran Sulaiman, Dublin (IE); Jansen Seheult, Dublin (IE); Frank Doyle, Dublin (IE); Ronan Conroy, Dublin (IE)

(73) Assignee: ROYAL COLLEGE OF SURGEONS IN IRELAND, Dublin (IE)

( * ) Notice: Subject to any disclaimer, the term of this patent is extended or adjusted under 35 U.S.C. 154(b) by 754 days.

(21) Appl. No.: 16/477,379

(22) PCT Filed: Jan. 10, 2018

(86) PCT No.: PCT/EP2018/050577
§ 371 (c)(1),
(2) Date: Jul. 11, 2019

(87) PCT Pub. No.: WO2018/130578
PCT Pub. Date: Jul. 19, 2018

(65) Prior Publication Data
US 2020/0022647 A1 Jan. 23, 2020

(30) Foreign Application Priority Data
Jan. 11, 2017 (EP) ..................................... 17151063

(51) Int. Cl.
*A61B 5/00* (2006.01)
*A61J 7/04* (2006.01)
*G16H 10/60* (2018.01)

(52) U.S. Cl.
CPC ............... *A61B 5/4833* (2013.01); *A61J 7/04* (2013.01); *G16H 10/60* (2018.01); *A61J 2200/30* (2013.01)

(58) Field of Classification Search
CPC ......... A61B 5/4833; G16H 10/60; A61J 7/04; A61J 2200/30
See application file for complete search history.

(56) References Cited

U.S. PATENT DOCUMENTS 10,285,638 B2 * 5/2019 Jenkins ............... A61B 5/02405
10,791,987 B2 * 10/2020 Jenkins ................ A61B 5/0533
(Continued)

FOREIGN PATENT DOCUMENTS

WO 2003082096 A1 10/2003

OTHER PUBLICATIONS

Choo et al. "Derivation of adherence metrics from electronic dosing records." Journal of Clinical Epidemiology 54(6): 619-626 (2001).
(Continued)

*Primary Examiner* — Michael Collins
(74) *Attorney, Agent, or Firm* — NIXON PEABODY LLP; David S. Resnick; Sorinel I. Cimpoes

(57) ABSTRACT

The present invention provides a method for monitoring adherence by a patient to a medication. The method comprises the steps of obtaining timing data in respect of each dose of a medication taken by a patient over a time interval, estimating the concentration of the medication in the patient's body over the time interval based on the dose timing data; determining the proportion of time over the time interval the concentration of the medication in the patient's body exceeds a target concentration; and calculating an adherence score for the patient based on the determined proportion of time the concentration of the medication in the patient's body exceeds the target concentration.

13 Claims, 4 Drawing Sheets

(56) References Cited

U.S. PATENT DOCUMENTS

| | | | |
|---|---|---|---|
| 11,193,925 B2* | 12/2021 | Dennis | A61B 5/0836 |
| 2007/0060819 A1* | 3/2007 | Altshuler | A61B 5/6843 |
| | | | 600/475 |
| 2007/0172424 A1* | 7/2007 | Roser | A61B 5/1455 |
| | | | 424/9.1 |
| 2007/0224128 A1* | 9/2007 | Dennis | A61B 5/4839 |
| | | | 73/23.3 |
| 2010/0255598 A1* | 10/2010 | Melker | A61K 51/1206 |
| | | | 436/144 |
| 2013/0131586 A1* | 5/2013 | Poutiatine | H01Q 1/2208 |
| | | | 604/59 |
| 2013/0276785 A1* | 10/2013 | Melker | A61M 16/0677 |
| | | | 128/204.23 |
| 2016/0356763 A1* | 12/2016 | Jenkins | G06N 3/12 |
| 2016/0357924 A1* | 12/2016 | Jenkins | A61B 5/4833 |
| 2020/0297955 A1* | 9/2020 | Shouldice | G16H 50/70 |
| 2021/0283021 A1* | 9/2021 | Elia | A61J 15/0084 |

OTHER PUBLICATIONS

Morrison et al. Defining medication adherence in individual patients. Patient Preference and Adherence 9: 893-897 (2015).
Sulaiman et al. "A Method to Calculate Adherence to Inhaled Therapy that Reflects the Changes in Clinical Features of Asthma." Annals of the American Thoratic Society 13(11): 1894-1903 (2016).

\* cited by examiner

| Parameter | Peak Flow | A.E rate |
|---|---|---|
| $\alpha$ | 0.062 ($T_{\frac{1}{2}}$ = 11.2 hrs) | 0.056 ($T_{\frac{1}{2}}$ = 12.4 hrs) |
| $\beta$ | 63 | 50-100 |
| $\theta$ | 0.56 | 0.69 |
| $\tau$ | 18.2 hrs | n/ahrs |

(a)

| Error Type | $\delta$ |
|---|---|
| None | 1.0 |
| Low inspiratory flow rate (PIFR < 35 L/min) | 0.7 |
| Exhalation error (patient exhales into inhaler) | 0.5 |
| Low PFIR + Exhalation error | 0.35 |
| No blister detected (drug not released) | 0 |
| No inhalation detected | 0 |

METHOD FOR MONITORING ADHERENCE TO MEDICATION

CROSS-REFERENCE TO RELATED APPLICATIONS

This application is a 35 U.S.C. § 371 National Phase Entry Application of International Application No. PCT/EP2018/050577 filed Jan. 10, 2018, which designates the U.S. and claims benefit under 35 U.S.C. § 119 (a) of EP Provisional Application 17/151,063.9 filed Jan. 11, 2017, the contents of which are incorporated herein by reference in their entireties.

FIELD

The present invention is concerned with a method for monitoring adherence to medication. More particularly, the invention is concerned with a method for monitoring adherence to medication in terms of the maintained drug concentration in a patient's body over a particular time interval.

BACKGROUND

Assessing patient adherence to medication is a perennial problem in the management of many chronic illnesses. The ability to properly assess adherence is essential in accurately measuring the effectiveness of a course of treatment. This is an issue in the case of many drug delivery systems, where errors in technique can result in a patient receiving a drastically reduced dose (for example aerosol delivery systems such as inhalers). In addition, the effectiveness of many medications may depend on correct timing and spacing of doses, which must be accounted for in order to assess the patient's response to treatment. Measurement of adherence may also play an important role in the prescription of medication, since a non-adherent patient may in practice receive a significantly lower dose than intended.

Currently used methods of adherence assessment include self-report, dose counting (using patient diaries or dose counting devices attached to drug delivery systems) and assessment of patient prescription refill rates. Each of these methods have numerous drawbacks, and in some cases, bear little or no relation to actual adherence behaviour. In particular, patient self-reported adherence has been shown to have little or no correlation with health outcomes, and indeed, is found to have a low correlation with more objective measures of adherence. This may be a result of memory problems, an unwillingness to admit to non-adherence, or any number of other physical and psychological factors.

It will be appreciated that methods such as dose counting and prescription refill monitoring are more objective than self-report. However, such methods are still prone to many sources of error. Prescription refill data, for example, does not provide any evidence as to whether the medication was actually taken. Furthermore, neither prescription refill nor dose counting give any estimate of the timing or proficiency with which the dosage was received. For example, some patients display multi-dosing behaviour, where several doses are taken together, rather than being spaced out at regular intervals as prescribed. FIG. 1 shows an illustrative example of how the dose timing exhibited by two different patients may affect drug concentration. In both cases the patient has taken the same number of doses over the period shown. However in example (b) the patient displays erratic dose timing, with the result that the drug concentration in the patient's body drops below a target threshold concentration θ for approximately 50% of the period shown. In contrast, due to the fact that the patient took their dose at more regular intervals in example (a), it can be seen that the drug concentration in the patient's body remains above the target threshold concentration θ for the period shown. It will be appreciated that this may strongly alter the effectiveness of the treatment, while still leading to high adherence scores.

The paper by Alan Morrison et al entitled "Defining medication adherence in individual patients", Patient Preference and Adherence, vol. 9, 1 Jul. 2015, pages 893 to 897, describes a method for determining patient adherence which includes determining the proportion of time over a time interval an estimated concentration of medication in a patient's body exceeds a single hard threshold concentration value. This threshold concentration value was determined from pharmacokinetic models which did not take into account any patient variables or individual variability in treatment response or medication taking behaviour.

The paper by Imran Sulaiman et al entitled "A method to calculate adherence to inhaled therapy that reflects the changes in clinical features of asthma", Annals of the American Thoracic Society, 28 Jul. 2016, pages 1894 to 1903, simply describes the use of technique scores to weight doses of medication. There is no method described in this paper regarding the use of any type of threshold for determining patient adherence.

Thus, it is an object of the present invention to overcome at least one of the above mentioned problems.

SUMMARY

According to a first aspect of the invention, as set out in the appended claims, there is provided a method for monitoring adherence by a patient to a medication, the method comprising the steps of:
  obtaining timing data in respect of each dose of a medication taken by a patient over a time interval;
  calculating an estimate of the concentration of the medication in the patient's body over the time interval based on the dose timing data;
  determining the proportion of time over the time interval the estimated concentration of the medication in the patient's body exceeds a target concentration by applying a continuous threshold function to the estimated concentration of the medication in the patient's body over the time interval; and
  calculating an adherence score for the patient from the output of the threshold function over the time interval, wherein the adherence score represents the proportion of time the concentration of the medication is above the target concentration in the patient's body.

In an embodiment, the method further comprises the step of:
  obtaining in respect of each dose of the medication taken by the patient over the time interval a technique score representing the proportion of the full dose which was correctly taken by the patient; and
  wherein the step of estimating the concentration d(t) of the medication in the patient's body over the time interval comprises calculating the function:

$$d(t) = \sum_{t_s < t} \delta e^{-a(t-t_s)}$$

wherein the data $\{t_s\}$ corresponds to the set of dose timing data, the parameter $\alpha$ corresponds to the decay rate of the medication, and the parameter $\delta$ corresponds to the technique score for each dose.

In one embodiment, the decay rate of the medication is calculated from the equation:

$$T_{1/2} = \frac{\ln 2}{\alpha}$$

wherein the parameter $T_{1/2}$ corresponds to the physiological half-life of the medication.

In another embodiment, the decay rate of the medication is estimated by a maximum-likelihood method.

In an embodiment, the method further comprises obtaining a value for the technique score by an analysis of the proficiency of the patient in respect of each dose taken.

In an embodiment, the technique score comprises a value of between 1 and 0, wherein 1 represents a correctly taken full dose and 0 represents an incorrectly taken full dose.

In an embodiment, the step of determining the proportion of time over the time interval the concentration of the medication in the patient's body exceeds a target concentration comprises applying a threshold function to the estimated concentration of the medication in the patient's body over the time interval, wherein the threshold function $\sigma(t)$ comprises:

$$\sigma(t) = \frac{1}{1 + e^{-\beta(d(t)-\theta)}}$$

wherein the parameter $\theta$ comprises a threshold concentration value corresponding to the concentration of the medication in the patient's body required to control the patient's medical condition and the parameter $\beta$ comprises a threshold sharpness value corresponding to the extent to which the adherence score depends on the threshold value.

In an embodiment, the threshold concentration value and the threshold sharpness value are determined from patient outcome data.

In an embodiment, the threshold concentration value and the threshold sharpness value are determined through the use of maximum likelihood estimation on the patient outcome data.

In an embodiment, the patient's medical condition is a respiratory disease, and wherein the patient data corresponds to peak expiratory flow rate data and adverse respiratory event data.

In an embodiment, the step of calculating an adherence score for the patient comprises averaging the output of the threshold function over the time interval to provide the adherence score.

In an embodiment, the adherence score comprises a value of between 0 and 1, which value represents the proportion of time over the time interval the concentration of the medication in the patient's body exceeds the target concentration.

In an embodiment, the step of calculating an adherence score for the patient comprises calculating a moving average of the threshold function to obtain a continuous measure of adherence over the time interval.

In an embodiment, the method further comprises providing a drug delivery system for delivering the medication to the patient, and further wherein the drug delivery system is adapted to obtain the dose timing data and the technique score.

In one embodiment, the drug delivery system comprises an aerosol delivery system.

In another embodiment, the drug delivery system comprises an injectable delivery system.

In yet another embodiment, the drug delivery system comprises a system for dispensing capsule medication.

In an embodiment, the method further comprises calculating based on the adherence score an estimate of the correct dosage of the medication required for the patient to control their medical condition.

In an embodiment, the threshold function comprises a sigmoidal threshold function comprising a plurality of parameters, wherein the value of at least one of the parameters of the threshold function is determined from patient outcome data.

In an embodiment, the method further comprises the step of:
obtaining in respect of each dose of the medication taken by the patient over the time interval a technique score representing an estimate of the proportion of the full dose which was received by the patient; and
wherein the step of calculating an estimate of the concentration $d(t)$ of the medication in the patient's body over the time interval comprises calculating the function:

$$d(t) = \sum_{t_s < t} \delta_{t_s} e^{-\alpha(t-t_s)}$$

wherein $\{t_s\}$ corresponds to the set of dose timing data obtained over the time interval, the parameter $\alpha$ corresponds to the decay rate of the medication, and the parameter $\delta$ corresponds to the technique score for each dose.

In an embodiment, the threshold function $\sigma(t)$ comprises:

$$\sigma(t) = \frac{1}{1 + e^{-\beta(d(t)-\theta)}}$$

wherein the parameter $\theta$ comprises a threshold concentration value corresponding to the concentration of the medication in the patient's body required to control the patient's medical condition and the parameter $\beta$ comprises a threshold sharpness value corresponding to the extent to which the adherence score depends on the threshold function, wherein the values of the parameter $\theta$ and the parameter $\beta$ are determined from patient outcome data.

In an embodiment, the method further comprises obtaining a value for the technique score by an analysis of information regarding the usage by the patient of a drug delivery device in respect of each dose taken.

In an embodiment, the technique score comprises a value of between 1 and 0, wherein 1 represents a full dose of medication received by the patient and 0 represents a dose where no medication was received by the patient.

In an embodiment, the technique score comprises a weighted score.

In an embodiment, the step of calculating an adherence score for the patient from the output of the threshold function over the time interval comprises integrating the output of the threshold function over the time interval to provide the adherence score.

In an embodiment, the step of calculating an adherence score for the patient from the output of the threshold function over the time interval comprises calculating a moving average of the threshold function to obtain a continuous measure of adherence over the time interval.

In an embodiment, the estimate of the correct dosage of the medication required for the patient to control their medical condition comprises the minimum dose required to maintain a concentration of the medication above the target concentration in the patient's body, and for the case where the patient takes all doses at the correct intervals the step of calculating the estimate of the correct dosage of medication comprises calculating by means of the equation:

$$\delta_r = \frac{-\theta(e^{-h\ln 2} - 1)}{e^{-h\ln 2}} = \frac{-(0.5^h - 1)}{0.5^h}\theta$$

wherein h comprises a constant representing the expected number of half-lives between doses.

In another aspect of the invention there is provided an apparatus for monitoring adherence by a patient to a medication, the apparatus comprising:
  means for obtaining timing data in respect of each dose of a medication taken by a patient over a time interval;
  means for calculating an estimate of the concentration of the medication in the patient's body over the time interval based on the dose timing data;
  means for determining the proportion of time over the time interval the estimated concentration of the medication in the patient's body exceeds a target concentration by applying a continuous threshold function to the estimated concentration of the medication in the patient's body over the time interval; and
  means for calculating an adherence score for the patient from the output of the threshold function over the time interval, wherein the adherence score represents the proportion of time the concentration of the medication is above the target concentration in the patient's body.

In another aspect of the invention there is provided a computer implemented system for monitoring adherence by a patient to a medication, the system configured with one or more modules to:
  obtain timing data in respect of each dose of a medication taken by a patient over a time interval;
  calculate an estimate of the concentration of the medication in the patient's body over the time interval based on the dose timing data;
  determine the proportion of time over the time interval the estimated concentration of the medication in the patient's body exceeds a target concentration by applying a continuous threshold function to the estimated concentration of the medication in the patient's body over the time interval; and
  calculate an adherence score for the patient from the output of the threshold function over the time interval, wherein the adherence score represents the proportion of time the concentration of the medication is above the target concentration in the patient's body.

In another aspect of the invention there is provided a method for monitoring adherence by a patient to a medication, the method comprising the steps of:
  obtaining timing data in respect of each dose of a medication taken by a patient over a time interval;
  estimating the concentration of the medication in the patient's body over the time interval based on the dose timing data;
  determining the proportion of time over the time interval the concentration of the medication in the patient's body exceeds a target concentration; and
  calculating an adherence score for the patient based on the determined proportion of time the concentration of the medication in the patient's body exceeds the target concentration.

In another aspect of the invention there is provided an apparatus for monitoring adherence by a patient to a medication, the apparatus comprising:
  means for obtaining timing data in respect of each dose of a medication taken by a patient over a time interval;
  means for estimating the concentration of the medication in the patient's body over the time interval based on the dose timing data;
  means for determining the proportion of time over the time interval the concentration of the medication in the patient's body exceeds a target concentration; and
  means for calculating an adherence score for the patient based on the determined proportion of time the concentration of the medication in the patient's body exceeds the target concentration.

In another aspect of the invention there is provided a system for monitoring adherence by a patient to a medication, the system configured with one or more modules to:
  obtain timing data in respect of each dose of a medication taken by a patient over a time interval;
  estimate the concentration of the medication in the patient's body over the time interval based on the dose timing data;
  determine the proportion of time over the time interval the concentration of the medication in the patient's body exceeds a target concentration; and
  calculate an adherence score for the patient based on the determined proportion of time the concentration of the medication in the patient's body exceeds the target concentration.

BRIEF DESCRIPTION OF THE DRAWINGS

The invention will be more clearly understood from the following description of an embodiment thereof, given by way of example only, with reference to the accompanying drawings, in which:

FIG. 4(a) shows exemplary fitted parameter values α, β, θ and τ for use with the method of the invention when the method is being performed in respect of patients having a respiratory disease such as asthma, the parameters obtained using the measurements of Peak Inspiratory Flow Rate (PIFR) and Adverse event rate (AE rate) respectively as target outcomes, while FIG. 4(b) shows exemplary values of the parameter δ corresponding to particular technique errors exhibited by this exemplary patient dataset.

DETAILED DESCRIPTION OF THE DRAWINGS

It will be appreciated that the aim of medication is to maintain a certain concentration of the medication in a patient's body or system in order to treat the patient's medical condition. Thus, the present invention defines a method for monitoring a patient's adherence to their medication in terms of the maintained drug concentration in their body over a particular time interval.

The method comprises the steps of obtaining timing data in respect of each dose of a medication taken by a patient over a time interval; calculating an estimate of the concentration of the medication in the patient's body over the time interval based on the dose timing data; determining the proportion of time over the time interval the estimated concentration of the medication in the patient's body exceeds a target concentration by applying a continuous threshold function to the estimated concentration of the medication in the patient's body over the time interval; and calculating an adherence score for the patient from the output of the threshold function over the time interval, wherein the adherence score represents the proportion of time the concentration of the medication is above the target concentration in the patient's body. The threshold function comprises a sigmoidal model which has parameters whose values are optimised for each patient from the patient's individual outcome data.

Figure 1:
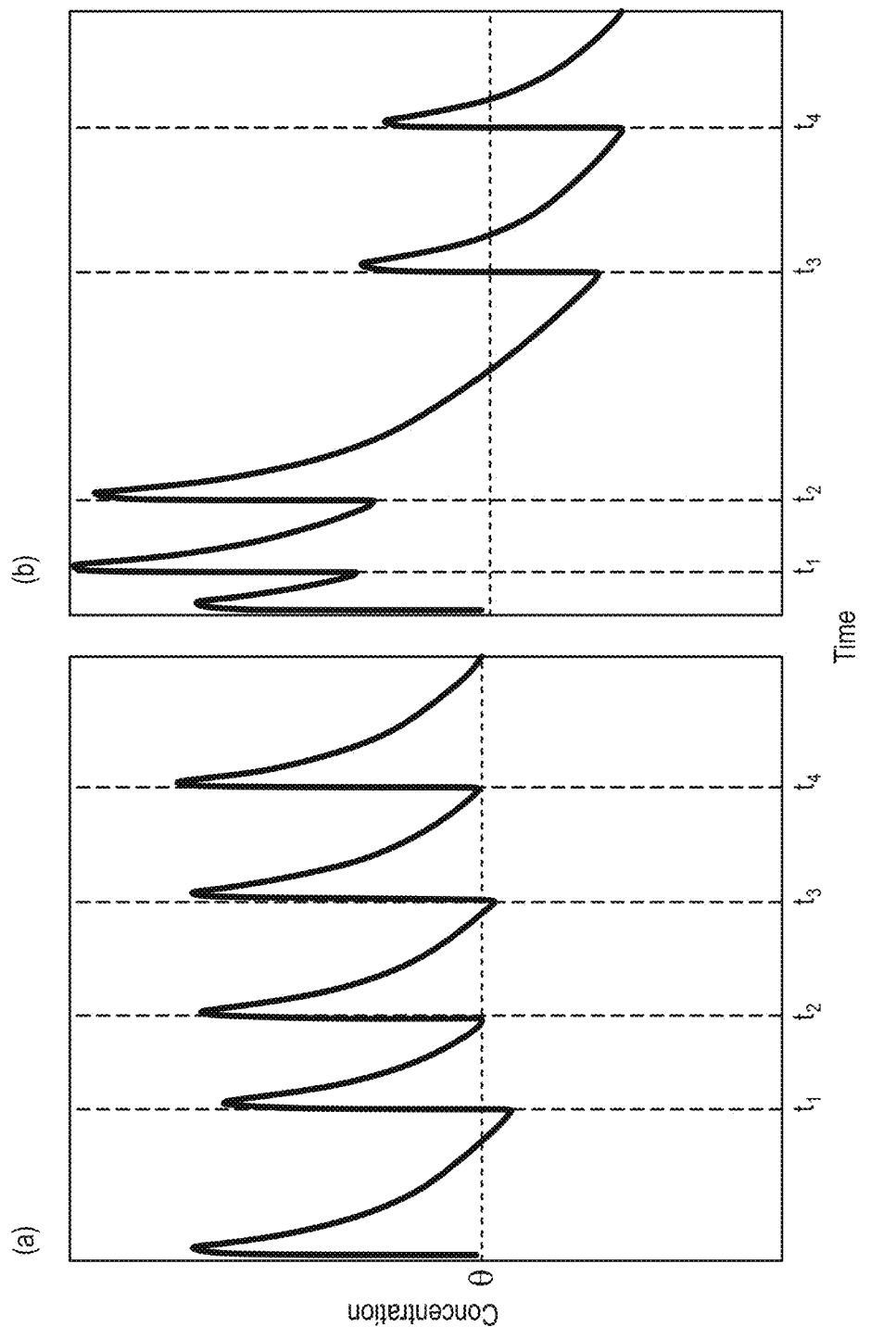
FIG. 1 shows exemplary simulated drug concentrations for two patients, with target threshold concentration θ.
Figure 2:
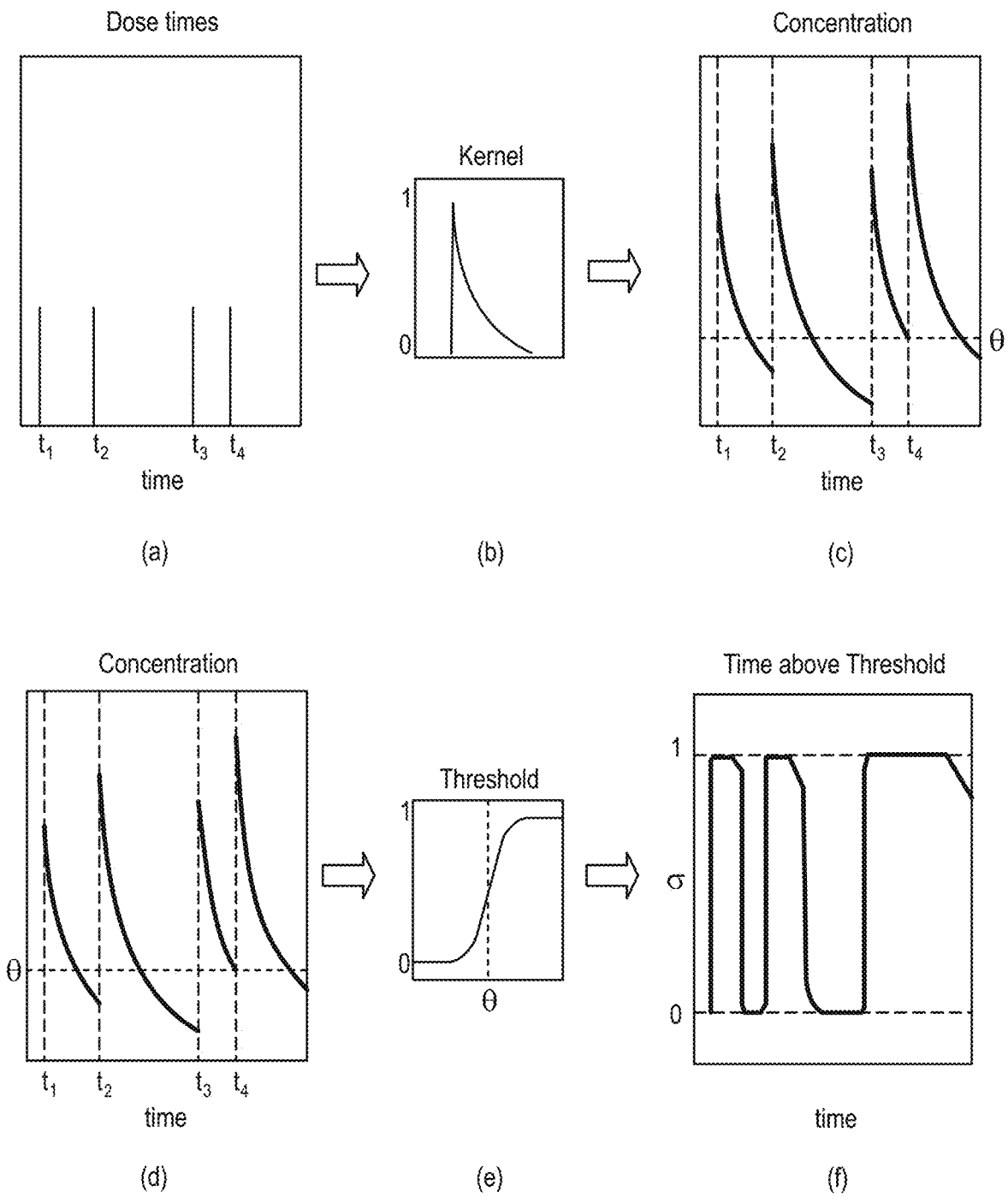
FIG. 2 shows a schematic of the main steps involved in the time-above-threshold calculation provided by the method of the present invention.

The timing data in respect of each dose of medication taken by a patient over a predetermined time interval may be obtained in any suitable manner, in order to obtain a dose timing dataset $\{t_s\}$ which contains a set of weighted dose times which correspond to the time of each dose of medication taken by a patient over the time interval, such as for example $\{t_1, t_2, t_3, t_4\}$, as shown in FIG. 2(a). In one embodiment, the timing data in respect of each dose may be obtained by a device attached to the drug delivery system being used by the patient to receive the medication, such as for example a device which is configured to record the time corresponding to each dose taken by the patient over the time interval. The drug delivery system may be of any known type. The drug delivery system could be an aerosol drug delivery system, such as for example an inhaler, in the case where a patient suffers from respiratory illness. The drug delivery system could alternatively be an injectable delivery system, such as for example an insulin pen, in the case where a patient is a diabetic. Alternatively, the drug delivery system could be a system for dispensing any type of tablet or capsule medication.

The calculation of the estimate of the concentration of the medication in the patient's body over the time interval based on the dose timing dataset is performed by modelling the time course of concentration for the particular medication being taken by the patient.

In accordance with the present invention, the concentration d(t) is given by the exponential function $$d(t) = \sum_{t_s < t} \delta_{t_s} e^{-\alpha(t-t_s)} \quad (1)$$

More generally, depending on the pharmacodynamics and delivery method of the drug in question, the concentration model may be adjusted to account for parameters such as different absorption and elimination rates. In this case, the concentration may be given by one of a family of functions of the form:

$$d(t) = \sum_{t_s < t} \delta_{t_s} (t-t_s)^{p_1} e^{-\alpha(t-t_s)^{p_2}+1}$$

Where the powers $p_1$ and $p_2$ are parameters that encode how the drug is metabolised in the system.

FIG. 2b illustrates an exemplary concentration profile for a single dose of medication, while FIG. 2c illustrates how the estimated concentration d(t) of the drug in the patient's body over time given by the function in equation (1) is a combination of the weighted dose times and the concentration profile for a single dose. In these equations, $\{t_s\}$ corresponds to the dataset of dose times associated with the patient, such as for example the set of dose times which was obtained over a predetermined time interval by the drug delivery system being used by the patient to administer their medication, as discussed above. The parameter α represents the decay rate of the medication in question. In one embodiment, the decay rate is calculated is by the equation:

$$T_{1/2} = \frac{\ln 2}{\alpha} \quad (2)$$

where $T_{1/2}$ corresponds to the physiological half-life of the medication in question. In an alternative embodiment, the decay rate can be estimated through the use of maximum likelihood methods.

The parameter δ is a technique score associated with each dose taken by the patient, which represents the estimated proportion of the full dose received by the patient in respect of each dose. The value of the technique score is determined based on data obtained regarding how proficiently the drug delivery device is being used by the patient.

The technique score parameter is necessary to obtain an accurate adherence score, as where there is technique error due to a patient's use of a particular drug delivery system, it can often lead to little or no actual dosage being received. In one embodiment of the invention, the technique score takes the value of 1 for correctly taken doses, and values of between 0 and 1 for doses where technique errors were made. In another embodiment of the invention, the technique score could comprise a weighted score, such as for example a weighted score calculated from the inspiratory flow rate of a patient.

The technique score can be obtained by an analysis by the drug delivery system and an analysis of the proficiency of the patient in respect of each dose taken. For example, where the drug is delivered by an inhaler, data such as how well the inhaler was primed by the patient, whether the patient exhaled before use, and the inspiratory flow rate achieved on each use can be obtained in respect of each dose taken by the patient. Such exemplary data could be obtained for example through the use of a suitable tracking device. The obtained data is then used to calculate an estimate of the proportion of the full dose of the drug which is actually received by the patient at each dose. This calculation can be made for example with reference to a drug deposition curve, which characterises the proportion of drug absorbed as a function of inspiratory flow rate.

Since δ=1 for all correctly taken doses, independent of the actual dosage taken, it will be appreciated that the concentration, d(t), and the target threshold value, δ, are thus expressed in units of the prescribed dosage.

To determine the proportion of time spent above the target or threshold concentration for the predetermined time interval, the concentration value is then passed through a sigmoidal threshold transfer function, as illustrated in FIG. 2d. This results in the generation of a time above threshold function, an example of which is illustrated in FIG. 2e. As can be seen from FIG. 2*e*, this function is close to one when the drug concentration at a particular point in time is over the threshold concentration value and is close to zero when it is below the threshold concentration value.

In one embodiment, the sigmoidal threshold transfer function comprises the following logistic function:

$$\sigma(t) = \frac{1}{1 + e^{-\beta(d(t)-\theta)}} \quad (3)$$

The parameters $\theta$ and $\beta$ of the threshold function represent the threshold or reference drug concentration value and the sharpness of the threshold function respectively. That is, $\theta$ encodes the target drug concentration needed to control the medical condition of the patient, while the parameter $\beta$ captures how strongly the adherence score depends on the threshold function. It should be noted that this sigmoidal transfer function, $\sigma(t)$ is continuous with respect to both the concentration value, $d(t)$, and the model parameters $\theta$ and $\beta$.

Figure 3:
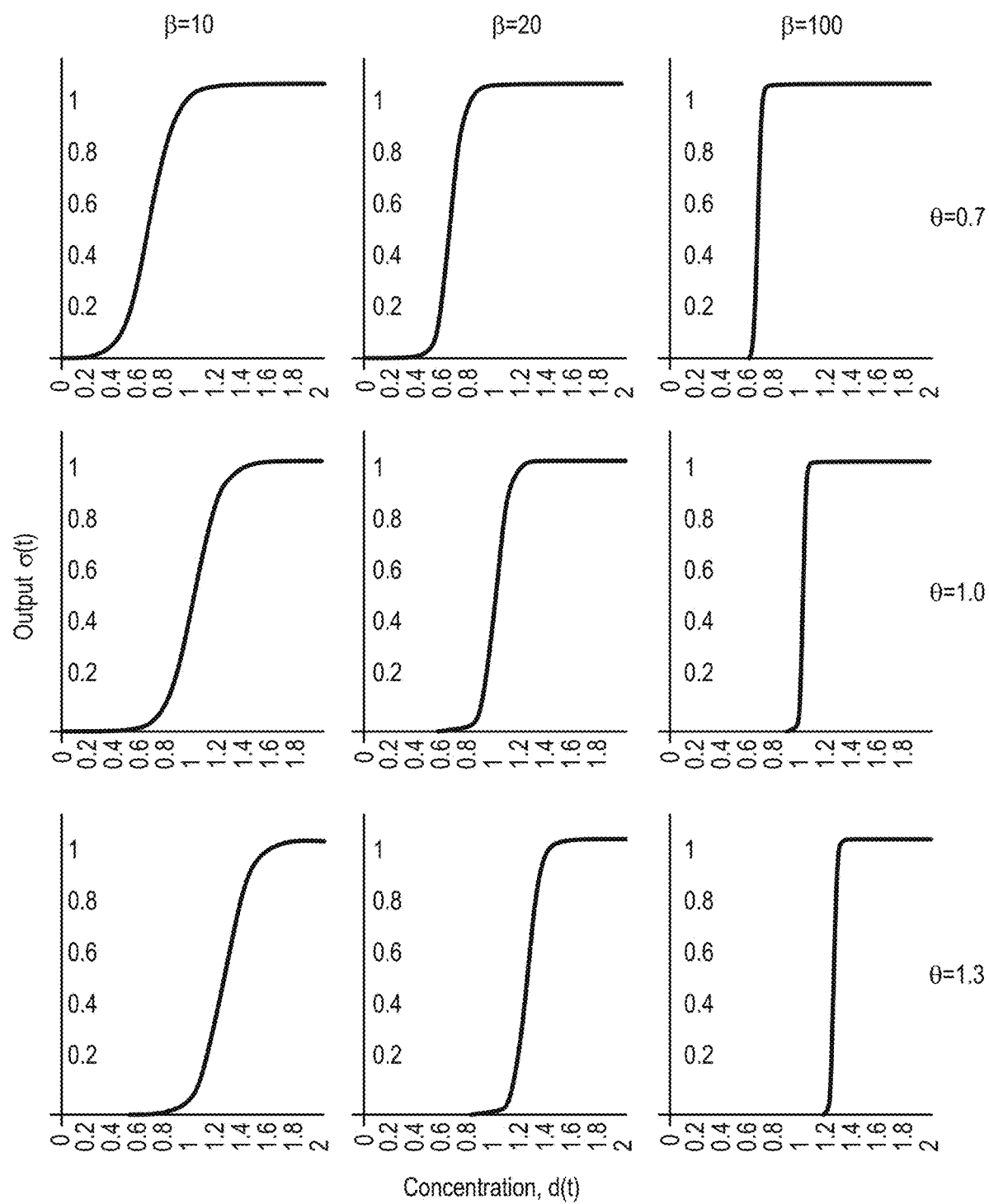
FIG. 3 illustrates the effects of different values of the parameters θ and β on the threshold function.

As can be seen from FIG. 3, for large values of $\beta$, the threshold function approximates a step function, with a value of 1 when the concentration is above the threshold concentration and 0 otherwise. For small values of $\beta$, the transition becomes smoother, and the threshold effect is weaker.

Any continuous sigmoidal threshold transfer function could equally well be used in place of the function shown above, provided the function possesses the following properties:

The value $\sigma(t)$ is in the interval [0,1] where $\sigma \to 1$ as $d(t) \to \infty$ $\sigma$ is a monotonic function of the concentration $d(t)$ (i.e., $\sigma$ always increases as $d(t)$ increases)

The function contains a parameter having the same dimension as the drug concentration, $d(t)$, representing a reference or target of the concentration (i.e. $\theta$ in the function above).

$\sigma$ is differentiable with respect to the concentration, $d(t)$, as well as with respect to any model parameters (e.g. $\beta$ and $\theta$ in the function above).

In one embodiment of the invention, the adherence score A for the clinically relevant time period (e.g. one month) is obtained by integrating the output of the threshold function over the time interval, giving a value of A between 0 and 1 representing the proportion of time above threshold:

$$A(\alpha, \beta, \theta) = \frac{1}{T} \int_0^T \sigma(t)dt \quad (4)$$

In an alternative embodiment, a moving average of the output $\sigma(t)$ may be employed to obtain a continuously varying measure of the current adherence score.

This adherence score enables a clinician to estimate the optimal drug doses in respect of an individual patient. The optimal dose can be calculated directly from the threshold value, and is defined as the minimum dose needed to maintain an above-threshold concentration, given the patient's threshold level and adherence pattern. For example, if the patient takes all doses at the correct intervals, then the optimal dose for the patient is simply given by the equation:

$$\delta_r = \frac{-\theta(e^{-h\ln 2} - 1)}{e^{-h\ln 2}} = \frac{-(0.5^h - 1)}{0.5^h}\theta$$

where h is a constant representing the expected number of half-lives between doses (for example, if the half-life is 12 hours and doses are to be taken twice daily, then h=1. Alternatively, if doses are to be taken once daily, then h=2 etc).

In one embodiment of the invention, the values of the parameters $\theta$ and $\beta$ of the threshold function are values which have been optimised against patients' health outcome data, in order to establish those values which give the best prediction of patient outcomes. The determination of the values is made from an analysis of patient data for the medication in question which may have been performed at any previous time.

The chosen values of these parameters are determined to be those values of the parameters $\theta$ and $\beta$ for which the adherence measure is most strongly predictive of patient outcomes. This is achieved by treating the adherence score as a predictor variable in a statistical model for the relevant outcome variable. Taking an example of where the outcome variable is the number of asthma exacerbations, the adherence score can be used as a predictor in a Poisson regression model, and where time to exacerbation/hospitalisation is the outcome (and therefore not all patients may have experienced the endpoint), a time-to-event model may be employed. Taking another example of where the outcome is a measure of lung function, the adherence score may be treated as a covariate in a time-lagged linear regression model.

It will be appreciated that since these statistical models are well defined, the likelihood function for these models may then be constructed as a function of the adherence score. As the adherence score has been defined to be continuously differentiable with respect to the model parameters of the threshold function (i.e. $\theta$ and $\beta$ in the exemplary threshold function of equation (3)), it is possible to determine the derivatives of the likelihood function with respect to these parameters, and hence to determine the values of the model parameters which maximise the likelihood of the data. This can be implemented using standard gradient descent techniques. Accordingly, such analysis typically involves the review of patient outcome data from a study of a group of patients having the same medical condition and who were prescribed the medication in question. For example, in the case where the method is being used to determine an adherence score for a patient having a respiratory disease such as an asthma patient or a patient having Chronic Obstructive Pulmonary Disease (COPD), the study may have involved gathering clinical data from a group of patients who were generally otherwise healthy. Thus, in this exemplary study, the patient outcome data could have comprised two established measures of patient well-being for patients having a respiratory disease, namely:

1. Peak Expiratory Flow Rate (PEFR), measured independently twice daily
2. The number of self-reported adverse respiratory events (AEs) within a one month period after the beginning of the adherence study.

These two measures correspond substantially to a continuous (daily) measure of lung function in the case of peak flow, and an overall measure of how well controlled a patient's condition is over a one month period in the case of the AE rate.

The threshold function parameters θ and β can then be obtained individually for each of these measures through the use of maximum likelihood estimation. When fitting against the AE rate, which is a summary measure covering a one-month period, the predictor used is the overall monthly adherence score (α, δ, β and θ). When fitting against daily peak flow data, a moving average adherence score may be used, with lag time τ, determined from the reverse correlation of peak flow against adherence.

FIG. 4 shows an exemplary table of (a) exemplary values of the parameters α, β, θ and τ, for use with the method of the invention when the method is being performed in respect of patients having a respiratory disease such as asthma. These parameters have been determined using the measured values of PEFR and AEs for an exemplary study on a patient dataset having asthma, while FIG. 4(b) shows exemplary values of the parameter δ corresponding to particular technique errors exhibited by this exemplary asthma patient dataset.

It should be understood by a skilled person that the nature of the study which is performed, along with the type of analysis undertaken from the study in order to determine the appropriate parameters θ and β of the threshold function to be used in the method of the present invention is therefore wholly dependent on the medication in respect of which the method of the invention is to be performed.

The present invention has many significant advantages over previously used methods of calculating adherence. Firstly, it explicitly captures the exponential decay of drug concentration in a patient's body. By contrast, many other methods implicitly assume that drug concentration is linear over time. Secondly, steroid medications, such as those used in inhalers, are known to exhibit threshold effects, whereby they are most effective only when a minimum concentration has been reached. The present invention specifically accounts for such effects.

Furthermore, unlike standard measures of adherence, the present invention incorporates specific information about the delivery method, effectiveness and pharmaco-kinetics of the medication, and thus provides a very robust and sensitive measure of adherence. As the present invention precisely models the time course of the dosage concentration based on timing information, it can also account for missed doses and dose timing errors. Additionally, it can take account of technique error due to a patient's use of a particular drug delivery system.

The present invention also explicitly models the threshold concentration of medication needed to maintain good health. This is achieved through the use of a continuous sigmoidal threshold function, so that the parameters of the threshold function can be optimised from patient data. Thus, it enables an estimate to be made of the correct dosage required for an individual patient to achieve health, through the use of patient adherence data and outcomes.

The present invention also has the potential to greatly improve the statistical power of clinical drug trials. By de-convolving patient outcomes from their adherence behaviour, it is possible to obtain useful information even from those patients with poor adherence, and simultaneously remove a source of error from the dataset. As a result, the method of the present invention enables statistically significant estimates of treatment effectiveness to be obtained from smaller cohorts, so as to provide more efficient and cost effective clinical drug trials.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A computer-implemented method for treatment of a medical condition of a patient, the method comprising the steps of:
providing a computer coupled to a drug delivery system;
delivering a dose of a medication to the patient from the drug delivery system;
the computer reading timing data from a timing device coupled to the drug delivery system, the timing data indicating the delivery timings in respect of each dose of a medication which has been taken by a patient over a time interval;
the computer calculating an estimate of a concentration of the medication in the patient's body over the time interval based on the dose timing data; wherein the concentration, d(t), is estimated by a function:

$$d(t) = \sum_{t_s < t} \delta_{t_s}(t-t_s)^{p_1} e^{-\alpha(t-t_s)^{p_2}+1}$$

where $\{t_s\}$ is the set of dose timing data, α is the decay rate of the medication, $p_1$ and $p_2$ are constant exponents, and $\delta_{t_s}, \delta_{t_s} \in [0,1]$, is the technique score associated with each dose of the medication which was taken by the patient over the time interval, wherein the technique score represents an estimate of a proportion of a full dose which was received by the patient based on proficiency data from delivery of the dose of the medication measured by a tracking device of the drug delivery system;
the computer determining the proportion of time over the time interval for which the estimated concentration of the medication in the patient's body exceeds a target concentration, θ, by applying a continuous sigmodal threshold function, σ(t), to the estimated concentration of the medication in the patient's body over the time interval-via the computer wherein the threshold function has the following properties:
σ(t) ∈ [0,1];
σ(t)→1 as d(t)→∞;
σ(t) increases monotonically with d(t) in such a way that σ(t)≈1 when d(t)»θ and σ(t)≈0 when d(t)«θ; and
the threshold function contains a parameter β such that as β→∞ the threshold function approaches the step function:

$$\sigma_{step}(t) = \begin{cases} 1, & d(t) \geq \theta \\ 0, & d(t) < \theta \end{cases};$$

the computer calculating an adherence score for the patient over the time interval-via the computer, wherein the adherence score represents the proportion of time for which the concentration of the medication is above the target concentration in the patient's body, wherein the adherence score is calculated either by integrating the threshold function over the time interval or by calculating a moving average of the threshold function to obtain a time-varying adherence score; and the computer estimating a correct dosage of the medication required for the patient to control a disease or a condition including a respiratory disease using a correct inhaler dosage or diabetes using a correct dosage of insulin, based on the adherence score and the drug delivery system delivering the correct dosage of the medication required for the patient to control their medical condition.

2. The method of claim 1, wherein the concentration d(t) is estimated by the function:

$$d(t) = \sum_{t_s < t} \delta_{t_s} e^{-\alpha(t-t_s)}$$

3. The method of claim 2, wherein the threshold function σ(t) comprises:

$$\sigma(t) = \frac{1}{1 + e^{-\beta(d(t)-\theta)}}$$

wherein the parameter θ comprises a threshold concentration value corresponding to the concentration of the medication in the patient's body required to control the patient's medical condition and the parameter β comprises a threshold sharpness value corresponding to the extent to which the adherence score depends on the threshold function, wherein the values of the parameter θ and the parameter β are determined from patient outcome data.

4. The method of claim 2, wherein the decay rate of the medication is calculated from the equation:

$$T_{1/2} = \frac{\ln 2}{\alpha}$$

wherein the parameter T1/2 corresponds to the physiological half-life of the medication.

5. The method of claim 2, wherein a value for the technique score was obtained by an analysis of information regarding the usage by the patient of a drug delivery device in respect of each dose taken.

6. The method of claim 5, wherein the technique score comprises a value of between 1 and 0, wherein 1 represents a full dose of medication received by the patient and 0 represents a dose where no medication was received by the patient.

7. The method of claim 5, wherein the technique score comprises a weighted score.

8. The method of claim 1, wherein the patient's medical condition is a respiratory disease, and wherein the patient outcome data corresponds to peak expiratory flow rate data and adverse respiratory event data.

9. The method of claim 1, wherein the step of calculating an adherence score for the patient from the output of the threshold function over the time interval comprises integrating the output of the threshold function over the time interval to provide the adherence score.

10. The method of claim 1, wherein the step of calculating an adherence score for the patient from the output of the threshold function over the time interval comprises calculating a moving average of the threshold function to obtain a continuous measure of adherence over the time interval.

11. The method of claim 1, wherein the estimate of the correct dosage of the medication, $\delta_r$, required for the patient to control their medical condition comprises the minimum dose required to maintain a concentration of the medication above the target concentration in the patient's body, and for the case where the patient takes all doses at the correct intervals the step of calculating the estimate of the correct dosage of medication comprises calculating by means of the equation:

$$\delta_r = \frac{-\theta(e^{-h\ln 2} - 1)}{e^{-h\ln 2}} = \frac{-(0.5^h - 1)}{0.5^h}\theta$$

wherein h comprises a constant representing the expected number of half-lives between doses.

12. An apparatus for treatment of a medical condition of a patient, the apparatus comprising:
a drug delivery device delivering the medication to the patient, the drug delivery device including a tracking device measuring proficiency data for each dose of medication delivered by the drug delivery device;
a timer device coupled to the drug delivery device outputting timing data for each dose of medication delivered by the drug delivery device;
a computer coupled to the drug delivery device, the computer operable to:
receive the timing data in respect of each dose of a medication taken by a patient over a time interval;
determine a technique score, $\delta_{t_s} \in [0,1]$, in respect of each dose of the medication taken by the patient over the time interval based on the proficiency data from the tracking device, the technique score representing an estimate of the proportion of the full dose which was received by the patient based on the proficiency data;
calculate an estimate of a concentration of the medication in the patient's body over the time interval based on the dose timing data, wherein the concentration, d(t), is estimated by a function:

$$d(t) = \sum_{t_s < t} \delta_{t_s}(t - t_s)^{p_1} e^{-\alpha(t-t_s)^{p_2}+1}$$

where $\{t_s\}$ is the set of dose timing data, α is the decay rate of the medication, $p_1$ and $p_2$ are constant exponents, and $\delta_{t_s}$ is the technique score;
determine the proportion of time over the time interval for which the estimated concentration of the medication in the patient's body exceeds a target concentration, θ, by applying a continuous sigmodal threshold function, σ(t), to the estimated concentration of the medication in the patient's body over the time interval wherein the threshold function has the following properties:
σ(t) ∈ [0,1];
σ(t)→1 as d(t)→∞;
σ(t) increases monotonically with d(t) in such a way that σ(t)≃1 when d(t)»θ and σ(t)≃0 when d(t)«θ; and
the threshold function contains a parameter β such that as β→∞ the threshold function approaches the step function:

$$\sigma_{step}(t) = \begin{cases} 1, & d(t) \geq \theta \\ 0, & d(t) < \theta \end{cases};$$

calculate an adherence score for the patient over the time interval, wherein the adherence score represents the proportion of time for which the concentration of the medication is above the target concentration in the patient's body, wherein the adherence score is calculated either by integrating the threshold function over the time interval or by calculating a moving average of the threshold function to obtain a time-varying adherence score; and estimate and deliver correct dosage of the medication required for the patient to control a disease or a condition including a respiratory disease using a correct inhaler dosage or diabetes using a correct dosage of insulin, based on the adherence score.

13. A computer implemented system for treatment of a medical condition of a patient, the system configured with one or more modules to:

deliver one or more doses of a medication to the patient from a drug delivery system;

receive timing data in respect of each dose of a medication which has been taken by a patient over a time interval, the timing data received from a timing device coupled to the drug delivery system, the timing data indicating the delivery of a dose of the medication to the patient from the drug delivery system;

receiving proficiency data from delivery of the dose of the medication measured by a tracking device of the drug delivery system;

calculate an estimate of a concentration of the medication in the patient's body over the time interval based on the dose timing data;

wherein the concentration, d(t), is estimated by one of a family of functions of the form:

$$d(t) = \sum_{t_s < t} \delta_{t_s} (t - t_s)^{p_1} e^{-\alpha(t-t_s)^{p_2} + 1}$$

or by the function:

$$d(t) = \sum_{t_s < t} \delta_{t_s} e^{-\alpha(t-t_s)}$$

where $\{t_s\}$ is the set of dose timing data, a is the decay rate of the medication, $p_1$ and $p_2$ are constant exponents, and $\delta_{t_s} \in [0,1]$, is the technique score associated with each dose of the medication which was taken by the patient over the time interval, wherein the technique score represents an estimate of the proportion of the full dose which was received by the patient based on the proficiency data;

determine the proportion of time over the time interval for which the estimated concentration of the medication in the patient's body exceeds a target concentration by applying a continuous threshold function $\sigma(t)$ to the estimated concentration of the medication in the patient's body over the time interval;

calculate an adherence score for the patient from the output of the threshold function over the time interval, wherein the adherence score represents the proportion of time for which the concentration of the medication is above the target concentration in the patient's body, wherein the threshold function comprises a sigmoidal threshold function comprising a plurality of parameters, wherein the value of at least one of the parameters of the threshold function is determined from patient outcome data; and estimate and deliver correct dosage of the medication required for the patient to control a disease or a condition including a respiratory disease using a correct inhaler dosage or diabetes using a correct dosage of insulin, based on the adherence score.

* * * * *